(12) United States Patent
Berg et al.

(10) Patent No.: US 8,476,452 B2
(45) Date of Patent: Jul. 2, 2013

(54) PROCESS FOR PREPARING 1,2-BENZOISOTHIAZOLINE-3-ONE

(75) Inventors: Carsten Berg, Borre (DK); Sangita Singh, Caterham (GB)

(73) Assignee: Titan Chemicals Limited, Tortola (VG)

( * ) Notice: Subject to any disclaimer, the term of this patent is extended or adjusted under 35 U.S.C. 154(b) by 34 days.

(21) Appl. No.: 13/281,600

(22) Filed: Oct. 26, 2011

(65) Prior Publication Data

US 2013/0109864 A1    May 2, 2013

(51) Int. Cl.
*C07D 275/04*    (2006.01)

(52) U.S. Cl.
USPC ........................................................ 548/209

(58) Field of Classification Search
USPC ........................................................ 548/209
See application file for complete search history.

(56) References Cited

U.S. PATENT DOCUMENTS 4,751,311 A * 6/1988 Backhouse ................... 548/209
4,915,943 A * 4/1990 Gago et al. ................ 424/93.46

FOREIGN PATENT DOCUMENTS

| CA | 1 269 985 | 6/1990 |
|---|---|---|
| EP | 1 498 508 | 1/2005 |
| JP | 06-345723 | 12/1994 |

OTHER PUBLICATIONS

Watanabe et al., CA 77:5209, 1972.*
Hinton et al., CA 56:55649, 1962.*
Siegemund A. et al., "1,2-Benzisothiazol-3(2H) . . . Biological Activity", Sulfur Reports, Harwood Academic Publishers, Chur, CH, vol. 23, No. 3,, Jan. 1, 2002, pp. 279-319 XP009165054.
Masao Shimizu et al., "Synthesis of . . . of Sulfenamides", Heterocycles, Elsevier Science Publishers B.V. Amsterdam, NL, vol. 60, No. 8, Jan. 1, 2003, pp. 1855-1864 XP001526085.

* cited by examiner

*Primary Examiner* — Laura L. Stockton
(74) *Attorney, Agent, or Firm* — Clark & Brody

(57) ABSTRACT

Sodium sulfide hydrate is at least partially dehydrated by heating with N-methyl 2-pyrrolidone. 2-chlorobenzamide is added to the mixture which is heated further. The mixture is cooled and treated with aqueous hydrogen peroxide to give the sodium salt of 1,2-benzoisothiazoline-3-one in good yield. Acidification if desired gives rise to the free 1,2-benzoisothiazoline-3-one.

3 Claims, No Drawings

PROCESS FOR PREPARING 1,2-BENZOISOTHIAZOLINE-3-ONE

This invention relates to processes for making 1,2-benzoisothiazoline-3-one which is sometimes known as "BIT" and has CAS #2634-33-5. BIT is a commercially important biocide.

CA 1 269 985 and U.S. Pat. No. 4,727,188 describe processes for preparing 1,2-benzoisothiazoline-3-ones. In a first step and as described in U.S. Pat. No. 4,727,188 anthranilamide is subjected to diazotisation by reaction with a nitrite (i.e. nitrate III) followed by reaction with sulfur dioxide to give 2,2'-dithiobenzamide. It is well known that diazotisation is implicated in the formation of nitrosoamines which can be a health hazard and the reaction is difficult to perform on an industrial scale. As an alternative to this reaction 2,2'-dithiobenzamides can be made from the corresponding acyl chloride but according to U.S. Pat. No. 4,727,188 this reaction is difficult to perform.

The ensuing benzothiamide is then subjected to oxidative ring closure of 2,2'-dithiobenzamide. The reaction is performed in alkaline conditions in the presence of oxygen or an oxygen donor such as a peracid as described in CA 1 269 985.

The invention seeks therefore to provide alternative process for the production of 1,2-benzoisothiazoline-3-one and salts thereof. It has now surprisingly been found that BIT can be produced in good yield by reaction of an alkali metal salt or ammonium salt (including mono-, di-, tri- and tetra-alkylammonium salts) of the corresponding 2-mercaptobenzamide with an oxidizing agent such as aqueous hydrogen peroxide. The resulting salt can then, if desired by converted to free 1,2-benzoisothiazoline-3-one by acidification.

2-Mercaptobenzamide is a known material. It is described for example in JP063457. According to that document 2-mercaptobenzamide can be made by the reaction of 2-halobenzamide with sodium sulfide. The authors of that document contend that when 2-chlorobenzamide is used as the starting material the yield of 2-mercaptobenzamide is 85%. No information of the purity of that material is given. The present inventors have repeated the process set forth in Example 1 of JP063457. The results are set forth herein and show that the yield of pure 2-mercaptobenzamide is low. Of the starting 2-chlorobenzamide only 43 mol % was converted into 2-chlorobenzamide. The reason for the large by-product fraction is believed to be due to the use of 60% sodium sulfide. The remainder of the crude sodium sulfide is water which hydrolyses the amide functionality of the benzamide. Commercially available sodium sulfide is available only as the hydrate and contains considerable water. It is not available cheaply in industrial useful amounts in anhydrous form. It is possible to produce anhydrous sodium sulphide in the lab by reaction of sodium with sulfur in liquid ammonia but this technique is too expensive for industrial scale use.

In accordance with an aspect of the invention in an initial step a sodium sulfide hydrate is slurried with N-methyl-2-pyrrolidone and heated in a dry atmosphere for example under dry nitrogen until at least some of the water is evaporated optionally with some of the N-methyl-2-pyrrolidone. Typical heating temperatures are between the boiling point of water and the boiling point of N-methyl-2-pyrrolidone at the pressure at which the transformation is taking place. At ambient pressure this implies a temperature in the range of about 100 to about 200° C. preferably the temperature is about 150, 160 or 170 to about 190 or 200° C.

Other polar aprotic solvents such as dimethyl sulfoxide, dimethylformamide, dioxane, hexamethylphosphorotriamide, tetrahydrofuran, sulfolane or 2-pyrrolidone can be used but in general much better results are obtained using N-methyl-2-pyrrolidone.

The dried sodium sulfide can be recovered but preferably is used directly for reaction with the halobenzamide. It is found that much less 2-chlorobenzoic acid is formed and next to no starting material remains unreacted than when untreated sodium sulfide hydrate is used. Additionally a small amount of the 2,2'-dithiobenzamide is formed. This is not a problem since 2,2'-dithiobenzamide itself undergoes oxidative cyclization to form BIT.

In principle these materials can be isolated by in practice it is not necessary. The resulting sodium salt of 2-mercaptobenzamide can then be oxidatively cyclised for example using hydrogen peroxide to give the sodium salt of the 1,2-benzoisothiazoline-3-one. Other suitable reagents for oxidative cyclisation may include potassium permanganate, ruthenium tetroxide, osmium tetroxide and organic peroxides such as MCPBA. The preferred oxidative cyclisation reagent is however an aqueous solution of hydrogen peroxide. Preferably the aqueous solution of hydrogen peroxide contains less than about 68 wt % hydrogen peroxide. Suitable concentrations may be in the range of about 3 wt % to about 68 wt % for example about 6 wt % to about 30 wt % such as about 10 to 20 wt % for example about 14 wt %. Generally the oxidative cyclisation is performed in N-methyl-2-pyrolidone. Other polar aprotic solvents such as dimethyl sulfoxide, dimethylformamide, dioxane, hexamethylphosphorotriamide, tetrahydrofuran, sulfolane or 2-pyrrolidone can be used but in general much better results are obtained using N-methyl-2-pyrrolidone.

Typically the reaction mixture containing the at least partially dried sodium sulfide is cooled to about 130° C. for example in the range about 120 to about 160° C. and then the benzamide compound is added. The mixture is then allowed to react. In order to speed the reaction it may be desirable to heat the mixture for example to a temperature in the range about 150 to about 190° C. If wished it is possibly to monitor progress of the reaction by for example HPLC.

When the reaction is sufficiently advanced the mixture is allowed to cool. Preferably any excess sodium sulfide is destroyed by adding a mineral acid such as hydrochloric acid and boiling until hydrogen sulfide evolution ceases. Aqueous hydrogen peroxide is added slowly and once all the peroxide has been added the mixture is worked up by distilling off the water and N-methylpyrrolidone.

The 1,2-benzoisothiazoline-3-one salt can be removed from the reaction mixture for use or can be converted to the 1,2-benzoisothiazoline-3-one by reaction with an acid such as hydrochloric acid.

While 2-chlorobenzamide is preferred on cost grounds to produce the 2-mercaptobenzamide it is also possible to use 2-bromobenzamide or other benzamides having a good leaving group such as sulfonic acids esters for example tosylates, mesylates and triflates at the 2-position.

Preferred embodiments of the invention are one-pot reactions in which initially sodium sulfide hydrate is heated with the polar aprotic solvent until sufficient water has been driven off (for example as determined by weight loss) then adding the benzamide and after a further period cooling the mixture and subjecting it to oxidative cyclisation.

Commercial sodium sulfide generally is supplied as the hydrate, $Na_2S \cdot xH_2O$, where the percentage of $Na_2S$ is specified. It is therefore a straightforward matter to calculate how much water is present in the sodium sulfide hydrate. Desirably it is heated with the N-methyl 2-pyrrolidone until much for example at least 50%, more preferably at least 60% such as at least 70% of the water for example at least 80% or at least 90% of the water is driven off. The skilled worker will have no difficulty in devising suitable methods for determining the amount of water present for example by using routine analytical techniques. In practice it may not be necessary to do this and the mixture can simply be heated for a long enough period.

While sodium sulfide is preferred other sulfides may be used. This will give rise to different BIT salts which may be useful.

EXAMPLE 1

Comparative

The process for synthesis of 2-mercaptobenzamide, set forth in example 1 of JP 06 3457 was repeated:

15.6 g (0.0983 mol) of 98% 2-chlorobenzamide, 16.0 g (0.1230 mol) of 60% sodium sulfide and 100 g N-methylpyrollidone (NMP) added to a 200 m13 neck flask provided with a stirrer, heated oil bath thermometer and condenser. The mixture was stirred at 160° C. for 4 hours.

NMP was distilled off at reduced pressure and the residue dissolved in 100 g of water.

The mixture was acidified to pH 2.0 by adding 35% hydrochloric acid at 20° C.

The separated crystalline material was isolated by filtration, washed with water and dried to constant weight of 11.6 g at 40° C.

HPLC analysis, calibrated by authentic samples, revealed the following composition of the isolated product:

(g; mol; molar % of theory): (1.2; 0.0071; 7.2) 2-chlorobenzamide, (2.8; 0.0177; 18.0) 2-chlorobenzoic acid and (6.5; 0.0424; 43.2) 2-mercaptobenzamide.

Based on weight the purity of 2-mercaptobenzamide is 56.0%.

EXAMPLE 2

Preparation of 1,2-benzoisothiazoline-3-one 23.4 g (0.12 mol) of 60% sodium sulfide (40% water) and 160 g N-methylpyrollidone (NMP) was added to a 200 m13 neck flask provided with a heated oil bath, stirrer and a thermometer. The mixture was stirred at 190° C. and purged with nitrogen to a weight loss of 25 g. To the dried slurry of sodium sulfide at 130° C., 18.1 g (0.117 mol), 2-chlorobenzamide was added and the mixture heated to 175° C. for 4 hours. HPLC analysis of the reaction mixture, calibrated with authentic samples showed (g; mol; molar % of theory): (0.37; 0.0012; 2) 2,2'-dithiodibenzoic acid and (16.5; 0.108; 88) 2-mercaptobenzamide 2-chlorobenzoic acid was not detected.

The mixture was cooled to 70° C., 40 g of water was added and pH adjusted to 3.0, by adding 28.5 g of 35% hydrochloric acid. The mixture is heated to boiling until excess of hydrogen sulphide is expelled. Expelled hydrogen sulphide is absorbed in a caustic solution. At 20° C., 27.0 g (0.111 mol) 14% hydrogen peroxide is introduced over 30 min.

Water and NMP is distilled off at reduced pressure and the residue is dissolved in 125 g of water. The water solution is acidified to pH 4 with 35% hydrochloric acid. Separated BIT crystals are filtered off, washed with water and air dried to constant weight. BIT yield 14.3 g (0.094 mol) which is 80.8% of theory. Purity 99.5% by HPLC.

The invention claimed is:

1. A process for preparing the sodium salt of 1,2-benzoisothiazoline-3-one comprising the steps of
   i) heating a mixture of sodium sulfide hydrate and N-methyl 2-pyrrolidone
   ii) distilling from said mixture water and optionally a portion of said N-methyl-2-pyrrolidone to leave a water-depleted mixture of sodium sulfide and said N-methyl-2-pyrrolidone,
   iii) adding at least one benzamide substituted at the 2-position with a good leaving group to the water-depleted mixture of sodium sulfide and N-methyl 2-pyrrolidone to give a mixture comprising 2-mercaptobenzamide and
   iv) subjecting the mixture comprising 2-mercaptobenzamide to oxidative cyclisation.

2. The process of claim 1 wherein the at least one benzamide substituted at the 2-position with a good leaving group is 2-chlorobenzamide.

3. The process of claim 1 wherein step iv) comprises contacting the 2-mercaptobenzamide with aqueous hydrogen peroxide.

* * * * *